United States Patent

Mariscotti

[11] Patent Number: 5,828,723
[45] Date of Patent: Oct. 27, 1998

[54] PROCESS FOR DETERMINING THE INTERNAL THREE-DIMENSIONAL STRUCTURE OF A BODY OPAQUE TO VISIBLE LIGHT BY MEANS OF RADIATIONS FROM A SINGLE SOURCE, SPECIALLY SUITABLE FOR REINFORCED CONCRETE PARTS

[75] Inventor: Mario A. J. Mariscotti, Bouloque, Argentina

[73] Assignee: Tomografia De Hormigon Armado S.A., Buenos Aires, Argentina

[21] Appl. No.: 601,763

[22] Filed: Feb. 15, 1996

[30] Foreign Application Priority Data

Feb. 15, 1995 [AR] Argentina ................................ 331.032

[51] Int. Cl.⁶ .................................................. G01N 23/02
[52] U.S. Cl. .............................................. 378/58; 378/901
[58] Field of Search ..................... 356/375, 376, 356/372; 250/559.22, 559.19, 559.29; 378/58, 901

[56] References Cited

U.S. PATENT DOCUMENTS 4,827,436  5/1989  Sabersky et al. ........................ 356/372
4,932,753  6/1990  Cohen .
5,124,914  6/1992  Grangeat .................................. 378/50

*Primary Examiner*—K. Hantis
*Attorney, Agent, or Firm*—Gottlieb, Rackman & Reisman, P.C.

[57] ABSTRACT

A non destructive method determines the three-dimensional structure of a body opaque to visible light, by means of radiations from a single body, particularly suitable for parts of a reinforced concrete structure, wherein the distance between the source and the sensitive plate is shorter than that of the prior art, and wherein the labor time at the body site is substantially less than that of the prior art. The steps of the method include, essentially, the following steps: making some previous assumptions, such as the circular shape of cross sections of iron rods within the concrete; placing in front of the body a source having a discrete cross section spaced therefrom a distance sufficiently small for producing on the two-dimensional image, apart from shadows, measurable penumbra zones; radiating the body for obtaining a two-dimensional image wherein shadow zones as well as penumbra zones may be distinguished, and quantifying the radiation influencing such zones; applying a method for measuring the radiation influencing the sensitive sheet following a set of parallel straight lines; and calculating by computer mathematical methods the geometrical arrangement on each plane of the different parts and materials.

13 Claims, 2 Drawing Sheets

PROCESS FOR DETERMINING THE INTERNAL THREE-DIMENSIONAL STRUCTURE OF A BODY OPAQUE TO VISIBLE LIGHT BY MEANS OF RADIATIONS FROM A SINGLE SOURCE, SPECIALLY SUITABLE FOR REINFORCED CONCRETE PARTS

FIELD OF THE INVENTION

The instant invention relates to a process for determining the three dimensional structure of a body opaque to visible light, by means of radiations from a single source. This process is particularly suitable for parts of a reinforced concrete structure, such as beams and columns.

Experimental work for this application has employed gamma radiation sources; however, it is possible that in the future, for this use or any other, other kinds of radiations will be more convenient, such as electromagnetic radiations or particle radiations.

It is assumed that the process will be suitable for other uses in construction, medicine, research, mechanics, etc. Up to now, it has been only tested in reinforced concrete structures.

PRIOR ART

Non-destructive methods for obtaining the internal structure of reinforced concrete have been known for several years. See "Recommendations for non-destructive methods of test for concrete. Part 3. Gamma radiography of concrete (BS 4408)", British Standards Institution, 1970, which is incorporated herein as a reference.

In the cited paper, as indicated by its title, different recommendations for obtaining the best results in gamma radiographs of concrete are cited. Some parts thereof, clearly defining the prior art are included hereinbelow.

Thus, two bi-dimensional techniques and a three-dimensional technique are disclosed.

The first one is for determining the existence of stresses and their location and approximate sizes. In this case, for obtaining borders with geometrical indefiniteness (which, as may be seen, are caused by penumbra) not higher than 0.75 mm, a formula and a table containing minimum distances between the source and the sensitive film are given, as a function of the source diameter and the distance between the object and the film. Thus, for a column of 450 mm depth (the distance from the object to the film is taken as a half of this depth when it is not known beforehand), and a source of 6 mm diameter, the distance between the source and the film is: 9.00×225 mm =2,025 mm.

The second technique is used for determining the size of hollow portions and for determining precisely the size and location of reinforcements. In this case, for the same example, the minimum distance between source and film is: 17.67×225 mm =3,976 mm.

None of the above mentioned techniques attains a three dimensional image; they are only used to observe flaws or other details regardless of their position related to depth.

Therefore, in order to obtain a two-dimensional image, the source should be spaced to such a distance not feasible in several constructions.

Concerning the other technique, in the British reference, at page 12, it is stated: "When neither size or position of reinforcement or defect is unknown, stereoscopic radiographs should be taken". And, according to literature of that time, stereoscopic meant precisely two or more radiographs taken from two or more different points.

Obviously, the minimum distances are the same as those of the second above mentioned technique.

On the other hand, improvements were attained in the techniques for improving contrast of the images obtained.

Contrast is impaired by radiation reflection on side objects, during reflection in objects located behind the body and in dispersion produced at the concrete itself.

According to known techniques, a better contrast is obtained by placing a radiograph film (sensitive sheet) between two plates made of a material capable of attenuating gamma radiations, such as lead plates, such as are referred to as reinforcing plates.

In fact, the front plate referred to therein attenuates or diminishes in a higher degree radiations reaching through angles which are very inclined with respect to the normal at the incidence point that those whose incidence is at less inclined angles. In fact, the latter are those which, coming from the source, run through the body under study, while the former ones are reflections from radiations influencing materials and peripheral parts on which they are reflected.

The rear plate attenuates two-fold the radiation influencing the sensitive sheet, which radiation is crossed through it. If the rear lead plate did not exist, this rear radiation would reflect on parts and materials behind the body under study and would again influence the sensitive sheet.

BACKGROUND OF THE INVENTION

In the photography art, it is known that for obtaining a three-dimensional image two photographs are required, taken from two different points (spaced at least some centimeters, simulating the position of human eyes) . Then, it seems impossible to obtain a three-dimensional image by means of a single projection. For example, U.S. Pat. No. 4,932,753 of Cohen describes a method of obtaining three dimensional stereoscopic views of an underground geological area to ascertain earthquake producing faults or buried archeological sites.

This, in fact, may not be so if some important factors are taken into account:

(1) In several three-dimensional structures (such as in the case of reinforced concrete) previous probable assumptions may be made. In the case of concrete, the assumption that the inner metal reinforcements are steel rods of circular cross section, is almost always true. Therefore, in a three-dimensional image obtained, the cylindrical shape of the rods is not obtained from the two-dimensional image obtained on the sensitive sheet, but from the previous assumption.

Another possible assumption is that into a column, rods have a dominating vertical direction, while into a beam, the dominating direction is longitudinal. This is not to be incorporated in the image, since there will be always some rods not having such dominating direction, but it serves for ordering a further exploration in the most suitable way.

2) In the prior art, developed when computers were not so powerful and were more expensive, results were directly obtained from the radiograph film, measuring thereon. This implied the requirement not only of high film resolution (this is also required with the method of the invention) but the shapes obtained, as a result of shadows of opaque radiation regions, had to have very precise or acute borders. Therefore, penumbra had to be eliminated, i.e. those regions illuminated only by a part of the radiant surface of the source or, likewise, the source had to be punctual, which implied a real source, having a certain diameter, at a high distance (as seen in the prior art references). This implied other problems: in several buildings, separating several meters from a column or beam implies having another column, beam or wall interposed.

On the other hand, at present it is possible to process images obtained on the sensitive sheet through a computer, for obtaining more precise images;

3) Due to point 2), it is evident that the use of penumbra was avoided or no use was made of penumbra. On the contrary, the present invention is directed to the production of penumbra zones which, as will be seen, give useful information for determining the position of different parts in depth.

4) In case of reinforced concrete explored specially through gamma radiation, but also in other cases, material most opaque to radiation (such as steel) is, however, partially penetrated by radiations. For example, the human observer experiments a phenomenon different from that of every day life with light, wherein the major part of opaque materials are sufficiently opaque to give a uniform shadow.

Gamma-radiographs for reinforced concrete give steel shadows with density variation along the cross sections thereof. This represents an advantage because it allows partial verification of the previous assumption that the rods' cross section is circular. This is partial since, although it does not allow ascertaining that the section is truly circular, it permits differentiating between a circular and a square section, for example.

But this also has a disadvantage in that if the shadow is not uniform, it is more difficult to separate the shadow region from the penumbra region, (i.e., the penumbra is never uniform)

However, according to the present invention, it will be seen that ways exist for finding their boundaries.

Advantages And Objects Of The Invention

The obtention of a three-dimensional image is very useful, since it is equivalent to determining the position and dimensions of the reinforcement. By means of a three-dimensional image, the position and diameter of iron rods of a concrete column allow checking, for example, the flexure stress to which the column is subjected to.

Further, the quantitative analysis of a two-dimensional image of the internal structure of a body forming part of a reinforced concrete construction, according to the prior art, is imprecise, since the parameter obtained quantitatively is not the actual diameter of each material but its projected diameter. Also, if the position of the material through depth is not known exactly, it is not possible to correct properly the projected diameter.

On the other hand, the obtention of a three-dimensional image by the prior art techniques implies (apart from the mathematical methods for obtaining it from two-dimensional images) double radiation from two different positions.

It is to be noted that, for obtaining each image, whether those of the prior art or those of the instant invention, several working hours of personnel highly skilled in handling a gamma radiation source are required. Of course, this time is employed in preparation, mounting, etc., apart from the radiation per se. The radiation time increases significantly with the thickness of the concrete part. Frequently, a projection takes up to a whole day. These extended durations of times have a great effect on the price of the service.

Therefore, with the novel method of the present invention, an average of half of the time is required than that required by the prior art.

Moreover, an object of the invention is to provide a non-destructive method for determining the three-dimensional structure of a body opaque to visible light.

A further object of the invention is to provide a method for determining the three-dimensional structure of a body opaque to visible light, by means of radiations from a single source.

Still another object of the invention is to provide a method for determining the three-dimensional structure of a body opaque to visible light specially to be applied to parts of a reinforced concrete structure, such as beams and columns.

A further object of the invention is to provide a method for determining the three-dimensional structure of a body opaque to visible light, wherein the distance between the source and the sensitive sheet is shorter than that of the prior art.

Still another object of the invention is to provide a method for determining the three-dimensional structure of a body opaque to visible light, wherein the duration of the working period at the site where the body is located is substantially shorter than that of the prior art.

SUMMARY OF THE INVENTION

In keeping with these objects and others which may become apparent, the present invention relates to a method for determining the three-dimensional structure of a body opaque to visible light, through radiations from a single source, of the type in which radiations from the source, after passing through said body, influence a sensitive sheet, located between two reinforcement plates, wherein a two-dimensional image formed by shadows caused by different opacities to said radiations of the different materials and parts of said internal structure is recorded. The source is capable of radiating in a limited radiation solid angle (for preventing radiation on other close bodies and loss of contrast due to reflections and dispersions from said near bodies), and is characterized by the following steps:

a) prior assumption of shapes, location and dimensions of the parts and materials of said internal structure;

b) placing on the peripheral parts of the body controls opaque to radiations and having known shapes and dimensions;

c) locating behind the body and attached thereto, a sheet sensitive to said radiations, between two reinforcing plates, and in front of the body a source of the type having a discrete cross section according to the dimensions assumed in step a), spaced therefrom a distance sufficiently short for producing at said two-dimensional image measurable penumbra zones, apart from the cited shadows;

d) radiating during an exposure time suitable for obtaining a two-dimensional image wherein shadow zones as well as penumbra zones may be distinguished, and quantifying the radiation influencing said zones;

e) applying a point to point measuring method for the radiation influencing the sensitive sheet following a set of parallel straight lines as a kind of scanning of said two-dimensional image, preferably in a direction perpendicular to the assumed dominating direction of step a), said point being spaced apart, selectively if required, such that at least 5 points be located at each penumbra zone, preferably 10 points;

f) computing, through mathematical methods applied on measurements of step e) on each line of the line set, with the aid of the shape of sections assumed in step a), of the shapes of the obtained two-dimensional image and from images obtained from controls of step b), the geometrical arrangement of each plane defined by each of said parallel straight lines and the source, of different parts and materials; the assembly of said geometrical arrangements forming the internal three-dimensional structure of the body.

The method of the invention is particularly suitable when said body is part of a reinforced concrete construction, such as a column, a slab, a partition or a beam, while said radiations are gamma radiations from a source of radioactive material in the form of a photon beam.

In step a) it is assumed that the metal internal part of the reinforced concrete body is comprised by circular cross section steel rods, having a dominating direction according to the function of said body in the whole construction (such as vertical direction for columns and longitudinal direction for beams).

This embodiment is preferred since between step d) and step e) there is an additional step for attaining by a computer the two-dimensional image obtained in step d), such that to each point obtained from said image correspond a pair of coordinates and a digitalized density value corresponding to its opacity. Step e) for measuring the incident radiation following a set of lines is carried out by a computer program. The assumed dominating direction of step a) is first checked visually. At the same time, step f) calculating the geometrical arrangement in each plane includes the following steps:

f1) density values obtained for a line of said set of lines are taken and plotted, thus obtaining an experimental curve;

f2) based on the experimental curve obtained in f1) detection zones of steel rods may be separated, and analyzed separately;

f3) each zone obtained in f2) is classified according to a visual inspection, classifying into simple or multiple rods, each zone including at least one rod;

f4) according to the class assigned, the corresponding theoretical formula is selected, which has constants, n parameters (depending on the class) and variables, such variables being the incident radiation in the form of a photon beam on the sensitive sheet, proportional to said density, and the abscissa on the sensitive sheets. the constants are the attenuation coefficients corresponding to concrete and iron, the distance between the source and the sensitive sheet, and other known data; and the n parameters as the central abscissa, the central ordinate and the radius of said at least one rod;

f5) the influencing radiation function is computed vs. the abscissa on the sensitive sheet, for a set of values of the n parameters, and then summation of the squares of differences between each experimental value obtained and the function computed for the same abscissa is obtained;

f6) values of n parameters are changed, each at a time, and f5) is repeated, directing changes towards the obtaining of a minimum of the summation obtained in point f5);

f7) once the minimum is obtained according to step f6) with a determined set of n parameters, this set of n parameters is taken as that corresponding to said at least one rod, this being determined by ordinate, abscissa and radius;

f8) this is repeated for the other zones separated at step f2), thus obtaining the geometrical arrangement corresponding to the plane defined by the line of step f1).

An alternative embodiment, not preferred, includes in step f) for computing the geometrical arrangement of each plane, the limit (boundary) between shadow zones of penumbra zones is determined deriving the opacity function of the sensitive sheet as a function of the position along each line of the lines set. The limit is located wherein the derivative is maximum in absolute value. The distance to the sensitive sheet from each part of the internal structure is obtained from the length on each line of the penumbra zone related to the distance between the source and the sensitive sheet and to the diameter of the cross section of the source. The diameter of the part is obtained relating the corresponding length on each line of the shadow zone related to the distance between the sensitive sheet and the source and the distance of said part to the sensitive sheet. For the shape of the part, the value assumed in point a) is taken, partially checked by the opacity distribution at the shadow zone of each line.

Based on experience, it is preferred that the cited sensitive sheet be a film of the photographic type, having between steps d) and e) a developing step; thus turning more clear the zones not receiving the radiation from said single source and more opaque those zones receiving said radiation; opacity and radiation influencing each of the surface elements being of continuously increasing related magnitudes, such that the opacity of each of the points is a measure of the radiation influencing the sensitive sheet. The point to point measuring method for radiation incident on the sensitive sheet in step e) includes a method for measuring opacity point to point.

In what concerns to the exposure time of step d), this could be estimated empirically as a function of the source intensity, the body thickness, the materials assumed in step a) and the sensitivity of said sensitive sheet.

However, it is preferred that the exposure time of step d) be determined according to the value indicated by a radiation meter located behind the sensitive sheet and to the sensitivity thereof.

In this embodiment, such radiation meter may be of the type integrating on a surface, such as a planar ionization chamber, or of the punctual type, such as a Geiger Muller meter.

BRIEF DESCRIPTION OF THE DRAWINGS

The invention will be hereinbelow described in connection with the accompanying drawings, which were drafted without a determined scale, and merely constitute illustrative exemplary embodiments of the invention to which users and those skilled in the art may add many alternatives and modifications without departing from the inventive spirit.

In all figures, the same reference numerals or letters correspond to similar or equivalent elements.

DETAILED DESCRIPTION OF THE INVENTION

Figure 2:
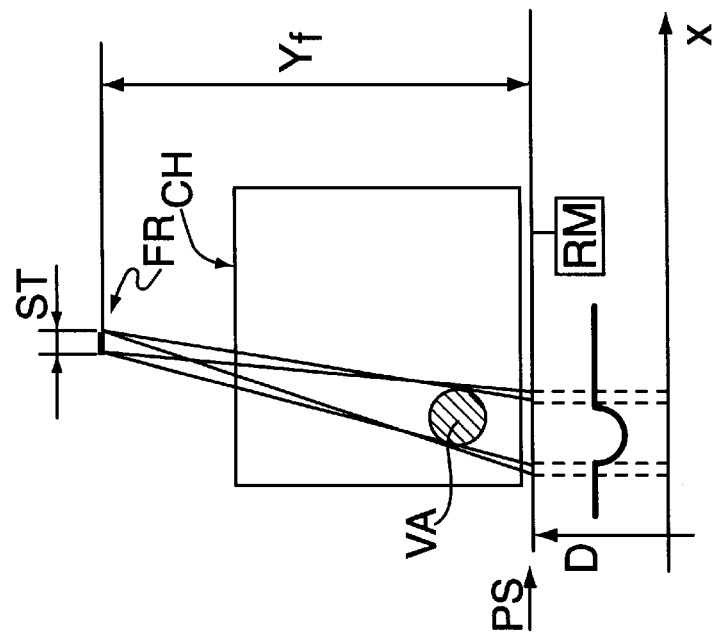
FIGS. 1 and 2 are diagrams which compare the radiation of a reinforced concrete column according to the prior art and to the instant invention.
Figure 1:
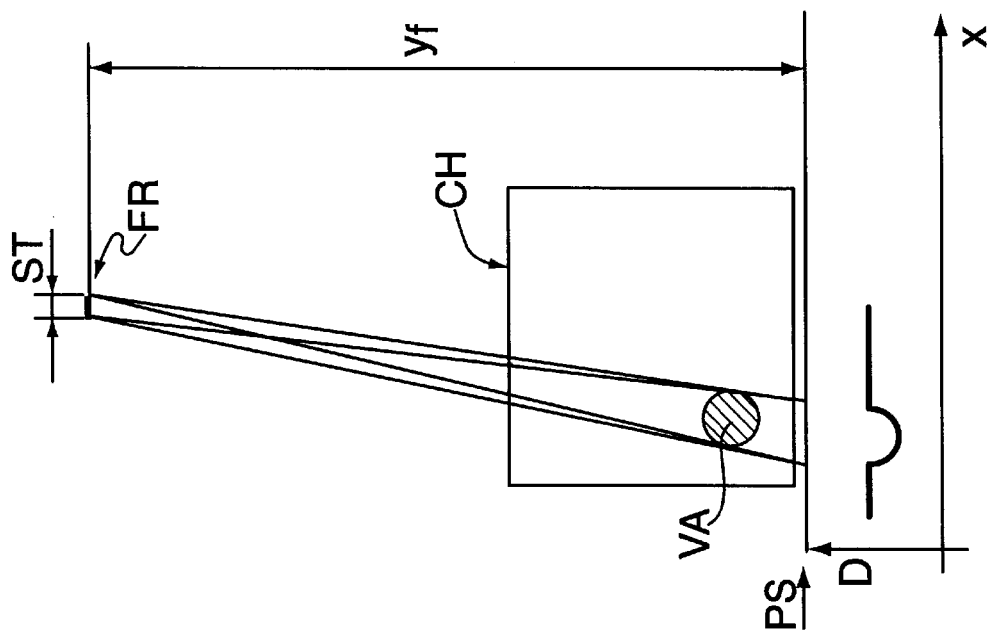

FIGS. 1 and 2 show the gamma radiation source =FR= having a cross section =ST=, a square reinforced concrete column =CH= wherein a single steel rod is included =VA= having circular cross section, and a sensitive sheet =PS= attached to the column at the face opposite to =FR=. Reinforcing plates are not shown in these figures since they are known by those skilled in the art and their function for the process of the invention is similar to that of prior art.

According to the prior art, shown in FIG. 1, distance =Yf= is larger than a minimum distance required for beams from the ends of cross section =ST= tangent to rod =VA= at each of their sides intersecting the sensitive sheet =PS= at very close points, such that they may be considered coincident at sight. Therefore, on the sensitive sheet (once developed) a neat image is obtained, since the penumbra zone is that corresponding to that between said two very close points.

According to the instant invention, shown in FIG. 2, the distance =Yf= should be shorter than a maximum distance and, therefore, smaller than that of the prior art, such that the penumbra region be sufficiently large to be measured. This results in the obtention of a less neat image, such that it has been prevented by the prior art techniques.

In both cases, the shadow region is that comprised between extreme penumbra regions.

In the Cartesian diagrams at the lower portion of FIGS. 1 and 2, density function (proportional to the opacity of the sensitive sheet) may be seen, which in the prior art case allows a less precise direct delimitation than that of the instant invention.

Figure 3:
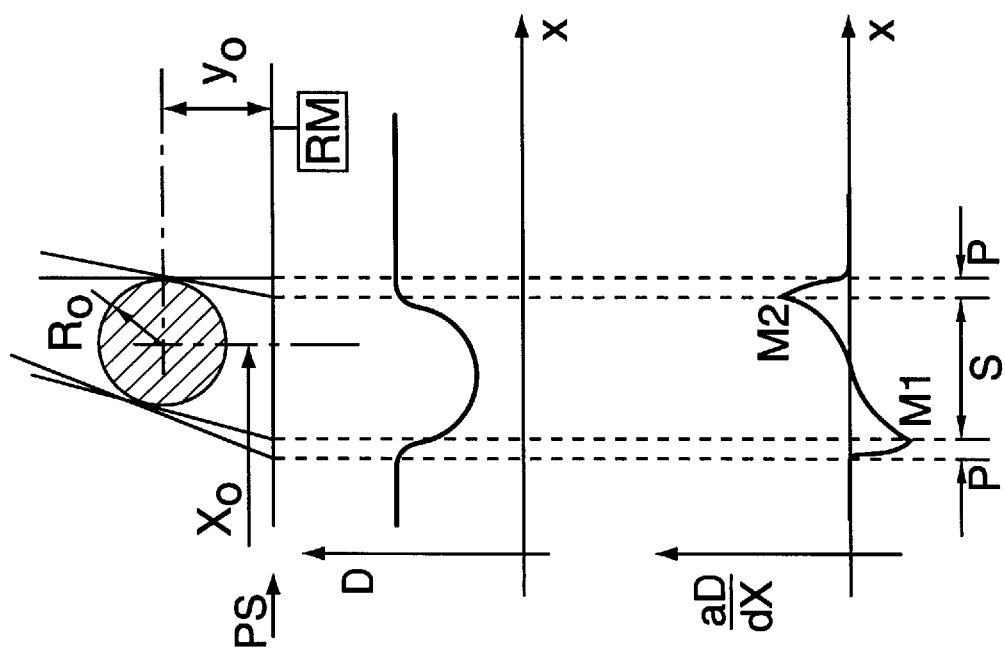
FIG. 3 is a diagram which shows Cartesian diagrams obtained from the image obtained from radiation, made according to FIG. 2, and widths of penumbra and shadow zones obtained through analysis thereof, according to a non-preferred alternative of the invention.

FIG. 3 shows in more detail diagram D as a function of x corresponding to FIG. 2, the precise limit between penumbra and shadow zones being not directly obtained.

According to one embodiment of the instant invention, by obtaining the density derivative with respect to x, the limit exists just in correspondence to the maximum =MI= and the minimum =M2= of said derivative (i.e., limits correspond to maximums in absolute value).

Therefore, penumbra =P= and shadow =S= zones are determined.

A better value of =S= may be obtained by measuring it not as indicated by FIG. 3, but between the centers of both zones =P=.

Through =P= ordinate =Yo= of the center of rod =VA= may be determined. In fact, through triangle similarity $$\frac{Yo}{Y_f - Y_o} = \frac{P}{ST}$$

wherein the only unknown value is Yo. =VA= diameter (or double radius =Ro=) is derived from $$\frac{2Ro}{Y_f - Y_o} = \frac{S}{Y_f}$$

and abscissa =Xo= of the center of =VA= is also obtained easily through triangle similarity.

This alternative may be implemented through a computer, loading the data corresponding to opacities of the sensitive sheet (already developed) by means of a specific digitalizer device (scanner). These devices are generally prepared based on a CCD type integrated circuit with a window on the photosensitive region, having different resolutions. When projecting on the photo-sensitive region the image obtained on the sensitive sheet, it should be taken into account that resolution thereof should be better than that of the CCD circuit, which in turn should allow quantification of at least 5 points at each penumbra zone. Sensitive sheet resolution is easily attained with common radiographic films, while resolution at penumbra zones on the CCD window is attained by varying reduction from the sensitive sheet.

This alternative was tested over several experiments, obtaining a relative degree of success, i.e., it is advantageous as compared to the prior art, but the results have not the desired precision obtained by the preferred embodiment.

It is assumed that any inaccuracy is the result of the logic dispersion of experimental data, not allowing the defining of the absolute maximum with precision.

However, this alternative demonstrates that penumbra zones are those containing the information which, once processed, allows determining the "depth" of each detected part. Mathematics allow obtaining this information in alternative ways, one of which is the basis of the preferred alternative which, although more indirect, permits better results.

The preferred embodiment is disclosed herein. In this alternative, the use of a computer is essential, since the amount of repetitive calculations if carried out otherwise would result in excessive cost.

In the instant disclosure, the positions on an axis of the plane on which the analysis is effected on the position of the sensitive sheet from an arbitrary O is designated abscissa or -X-, and positions in depth, measured from the sensitive sheet are designated Y.

The exposure time is adjusted, so that -shadows may be modulated by the steel thicknesses.

Density functions =D= corresponding to one, two, three, etc., rods, shadows of which are partially overlapped may be theoretically determined.

These functions or mathematical formula have two variables: abscissa X (independent variable) and density D (dependent variable); they have some constants, among them Yf (distance from the sensitive sheet to the source),$\mu$ fa and $\mu$ h. (attenuation coefficients for iron and cement corresponding to gamma energies employed, the thickness of the column under examination, etc.). ST is, in principle, also a constant, except for any difference given hereinbelow. These functions also have parameters, i.e., variables of each configuration; for example, if one is considering the case of the shadow isolated from a single rod, the parameters are: abscissa Xo of the rod center, ordinate Yo of the rod center, and the diameter or radius Ro of the rod. If consideration is given to the overlapped shadows of two rods, the amount n of parameters is duplicated, since they will be the abscissas, ordinates and radiuses of both rods, and so on.

Since complexity of the function increases with the number of parameters, the simplest case will be disclosed in this specification, that corresponding to a shadow isolated from a single rod.

Figure 4:
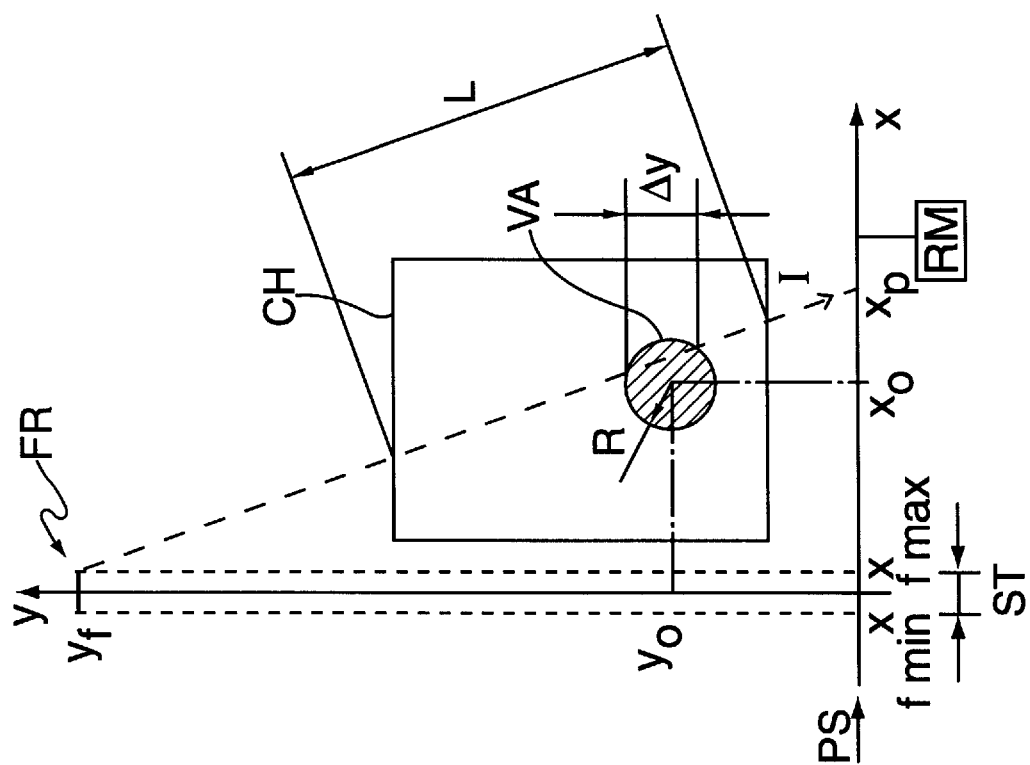
FIG. 4 is a diagram disclosing some symbols used in mathematical formula used in conjunction with the present invention.

As shown in FIG. 4, there is a single column =CH= in which circular cross section rod =VA= is located. The source extends from =Xfmin= to =Xfmax=. The other coordinate on the plane of the drawing is =Yf=, which, while being perpendicularly thereof (corresponding to the section drafted whose Z ordinate is null) is shifted a distance Zf (not shown).

If a photon beam of intensity Io is on an absorbent material for certain depth Y, the intensity is reduced to I, due to its interaction with atoms thereof. By increasing the distance Y by a differential dY, intensity I is reduced by dI. The probability of interaction per distance unit is (dI/I) (1/dY). This probability is called linear attenuation, which is generally designated with $\mu$ (as in *Morgan*, 1970). The probability of interaction of gamma radiation is related to the material density. With higher density a larger number of shocks is obtained, thus causing intensity decrease of the radiation transmitted. Thus:

$$-dI = \mu \, I \, dY.$$

The intensity reaching each point of the sheet is obtained by integration:

$$I(X_p) = \int B(X_f) \exp[(-\Delta Y)(\mu_{ee} - \mu n)\alpha :] . \exp(-\mu n L \alpha) \, d\,area \quad [1]$$

wherein: $B(X_p)$ is the factor considering the non uniform distribution effect of the source of gamma radiation, which is considered equal to 1 herein:

$\alpha$ is the factor considering inclination of gamma rays passing through the sample and which is equal to: $[1+(X_p-X_f)^2/Y_f^2]^{1/2}$ $X_f$ is the source abscissa;

$X_p$ is a generic point on the sensitive sheet;

$\Delta Y$ is the steel thickness covered by gamma rays; L is the concrete thickness (regardless the iron) crossed by radiation.

The integral extends on the source dimensions.

For determining $\Delta Y$ it is necessary to consider parameters related to the geometry of the configuration shown in FIG. 4, wherein steel rod =VA= has a radius R and its center is at $(X_o, Y_o)$; it is assumed that the source extends linearly from $X_{fmin}$ to $X_{fmax}$ and is at $(X_f, Y_f, Z_f)$.

Per similar triangles: $(X_p-X_i)/Y_i=(X_p-X_f)/Y_f$, besides: $R^2=(X_i-X_o)^2+(Y_i-y_o)^2$.

Solving for $X_i$ from the last equation and replacing it in the former one, one obtains a quadratic equation in $Y_i$:

$$Y_i^2 \left[ \frac{(X_p - X_f)^2}{Y_f^2} + 1 \right] - Y_i \left[ \frac{2(X_p - X_f)(X_p - X_o)}{Y_f} + 2Y_o \right] + (X_p - X_o)^2 - R^2 + Y_o^2 = 0$$

This equation has two roots, $Y_1$ and $Y_2$, which are the ordinates of the points wherein the considered beam intersects the circular section of rod =VA=; the difference $\Delta Y = Y_1 - Y_2$ is obtained as follows:

$$\Delta Y = \frac{\sqrt{b^2 - 4ac}}{a}$$

wherein a, b and c are coefficients of $Y_i^2$, if $Y_i$ and independent, respectively.

With expression [2] for Y, equation [1] may not be solved analytically, then the only way to solve it is through the numerical way. The integration is approximated by the following summation:

$$I(X_p) = \sum_{X_{fmin}}^{X_{fmax}} \exp[(-\Delta Y)(\mu_{fc} - \mu_u)\alpha]\exp(-\mu_u L\alpha) \quad [1$$

By selecting a reasonable amount of abscissas $X_f$ for effecting the summation, theoretical radiation (or theoretical density) influencing each point $X_p$ of the sensitive sheet for a determined set of n (in this case 3) parameters: R, $X_o$ and $Y_o$ is obtained.

Repeating this procedure with different parameter sets, once a theoretical curve very close to the experimental curve is obtained, one may say that the set of parameters is that corresponding to the actual situation.

The way of estimating the proximity between theoretical and experimental curves is by the minimum square method.

In other words, for each abscissa on which measurement (digitalization) of the image density on the sensitive sheet is effected, the difference between the experimental value and the corresponding theoretical value is computed; then the squares of all these differences are calculated and the squares are added. The theoretical curve closer to the experimental curve is that giving a minimum addition.

It is obvious that the amount of calculations required is so large that it may only be carried out by a computer. But, a computer, once the proper software is incorporated, very quickly effects these calculations as compared to the time involved for obtaining experimental results. These times are also of a short duration, as compared to those required for any other method based on the consideration of more than one gamma-graph for obtaining a three-dimensional image.

It is to be noted that the distance $X_{fmax} - X_{fmin} = ST$ of the source is not easy to measure. One of the ways of measuring this distance is using, each time the source is changed, an alternative of this procedure applied to a known structure, such that the only parameter will be =ST=, while R, $X_o$ and $Y_o$ will be data. Once the theoretical curve closer to the experimental curve is obtained, the value of =ST= employed will be considered correct (i.e. source calibration).

Radiation influencing penumbra zones P are measured by radiation meter RM engageable with sensitive sheet PS. Radiation meter RM may be of the type integrating one surface, such as a planar ionization chamber, or of the punctual type, such as a Geiger Muller meter.

An exemplary embodiment of the method for determining the internal three-dimensional structure of a body opaque to visible light, which is the main object of the invention, has been thus disclosed and the scope of protection of the present invention is basically defined by the annexed claims.

I claim:

1. A method for determining the three-dimensional structure of a body opaque to visible light, through radiations from a single source, of the type in which radiations from the source, after passing through said body, influence a sensitive sheet, located between two reinforcement plates, wherein a two-dimensional image formed by shadows caused by different opacities to said radiations of the different materials and parts of the internal structure is recorded, said source being capable of radiating in a limited radiation solid angle for preventing radiation on other close bodies and loss of contrast due to reflections and dispersions from said near bodies, comprising the following steps:

a) determining prior assumption of shapes, location and dimensions of the parts and materials of the internal structure;

b) placing on the peripheral parts of the body controls opaque to radiations, said controls having known shape and dimensions;

c) locating behind the body and attached thereto, a sheet sensitive to said radiations, between two reinforcing plates, and in front of the body a source of the type having a discrete cross section according to the dimensions assumed in step a), spaced therefrom a distance sufficiently short for producing two-dimensional image measurable penumbra zones, apart from said shadows;

d) radiating the body with penetrating radiation during a predetermined exposure time suitable for obtaining a two-dimensional image wherein shadow zones as well as penumbra zones may be distinguished, and quantifying the radiation influencing said zones;

e) applying a point to point measuring method for the radiation influencing the sensitive sheet following a set of parallel straight lines to scan said two-dimensional image, preferably in a direction perpendicular to the assumed dominating direction of step a), said point being spaced apart, selectively, such that a plurality of points are located at each penumbra zone;

f) computing, through mathematical methods applied on measurements of step a) on each line of the line set, with the aid of said assumed shape of said assumed structure assumed in step a), of shapes of said obtained two-dimensional image and from images obtained from controls of step b), a geometrical arrangement of each plane being defined by each of said parallel straight lines and the source, of different parts and materials; and assembling said geometrical arrangements of each of said planes forming the internal three-dimensional structure of the body.

2. The method for determining the three-dimensional structure of a body, as claimed in claim 1, wherein said body is part of a reinforced concrete construction, such as a column, a slab, a partition or a beam, wherein further said radiations are gamma radiations from a source of radioactive material in the form of a photon beam; wherein further in step a) it is assumed that the metal internal part of the reinforced concrete body is comprised of circular cross section steel rods, having a dominating direction according to the function of the body in the whole construction, including vertical direction for columns and longitudinal direction for beams.

3. The method for determining the three-dimensional structure of a body, as claimed in claim 1, wherein between step d) and step e) there is provided an additional step for attaining by a computer the two-dimensional image obtained in step d), wherein to each point obtained from said image there corresponds a pair of coordinates and a digitalized density value corresponding to an opacity of said image, wherein further step e) for measuring incident radiation of said radiation of said body, following a set of lines is carried out by a computer program, wherein an assumed dominating direction of step a) is first checked visually; while step f) calculating said geometrical arrangement in each said plane further comprises the following steps:

f1) determining density values obtained for a line of said set of lines are taken and plotted, thus obtaining an experimental curve;

f2) based on the experimental curve obtained in f1), detection zones of steel rods may be separated, and analyzed separately;

f3) classifying each zone obtained in f2) according to a visual inspection, and classifying into simple or multiple rods, each zone including at least one rod;

f4) according to the class assigned, selecting the corresponding theoretical formula, which said formula has constants, n parameters, depending on the class, and variables, said variables being the incident radiation in the form of a photon beam on the sensitive sheet, proportional to said density, and the abscissa on the sensitive sheet; the constants being the attenuation coefficients corresponding to concrete and iron, the distance between the source and the sensitive sheet, and other known data; and the n parameters being the central abscissa, the central ordinate and the radius of said at least one rod;

f5) computing the influencing radiation function as compared to the abscissa on the sensitive sheet, for a set of values of the n parameters, and then obtaining a summation of the squares of differences between each experimental value obtained and the function computed for the same abscissa;

f6) changing the values of n parameters each at a time, and repeating step f5), directing changes towards the obtaining of a minimum of the summation obtained in point f5);

f7) once the minimum is obtained according to step f6) with a determined set of n parameters, taking said set of n parameters as that corresponding to said at least one rod, this being determined by ordinate, abscissa and radius;

f8) repeating the above steps for the other zones separated at step f2), thus obtaining the geometrical arrangement corresponding to the plane defined by the line of step f1).

4. The method for determining the three-dimensional structure of a body, as claimed in claim 1, wherein in step f) for computing said geometrical arrangement of each plane, a limit boundary between respective shadow zones of penumbra zones is determined by deriving an opacity function of said sensitive sheet as a function of a position along each line of said lines set, said limit boundary being located wherein a derivative thereof is maximum in absolute value; obtaining the distance to the sensitive sheet from each part of the internal structure from the length on each line of the penumbra zone related to the distance between the source and the sensitive sheet and to the diameter of the cross section of the source; and obtaining the diameter of the part relating the corresponding length on each line of the shadow zone related to the distance between the sensitive sheet and the source and the distance of said part to the sensitive sheet; while for the shape of the part, taking the value assumed in point a), partially checked by the opacity distribution at the shadow zone of each line.

5. The method for determining the three-dimensional structure of a body, as claimed in claim 1, wherein said sensitive sheet is a film of the photographic type, having between steps d) and e) a developing step; thus turning more clear said zones not receiving said radiation from said single source and more opaque said zones receiving said radiation, said opacity and influencing said radiation on each surface elements of said body being of continuously increasing related magnitudes, such that said opacity of each points is a measure of said radiation influencing said sensitive sheet; said point to point measuring method for said radiation incident on the sensitive sheet in step e) including a method for measuring said opacity from a point to another point.

6. The method for determining the three-dimensional structure of a body, as claimed in claim 1, wherein the exposure time of step d), is estimated empirically as a function of a source intensity of said radiation, the body thickness, the materials assumed in step a) and the sensitivity of said sensitive sheet.

7. The method for determining the three-dimensional structure of a body, as claimed in claim 1, wherein the exposure time of step d) is determined according to the value indicated by a radiation meter located behind the sensitive sheet and to the sensitivity of said sensitive sheet.

8. The method for determining the three-dimensional structure of a body, as claimed in claim 1, wherein said radiation meter is of a type integrating measured radiation on a surface, such as a planar ionization chamber.

9. The method for determining the three-dimensional structure of a body, as claimed in claim 1, wherein said radiation meter is of a punctual type, such as a Geiger Muller meter.

10. The method of claim 1, wherein said discrete cross section extends in parallel with said sheet and has a source dimension and wherein said penumbra zones have a penumbra dimension dependent on said penumbra dimension, comprising the step of performing said computing using said penumbra dimension.

11. A method of obtaining a three-dimensional detailed image of the internal structure of steel reinforced concrete from a single source of penetrating radiation comprising the steps of:

a) exposing said steel reinforced concrete to penetrating radiation from a single source radiating a cross section of measurable dimensions;

b) placing radiation sensitive film on the opposite side of said steel reinforced concrete from said source to receive and record the attenuated radiation after passing through said concrete, said source and film being located at distances from said concrete so as to produce penumbra zones of measurable size on said film; and c) utilizing at least five points in each penumbra zone to generate data by computer of sufficient quantification to provide a three dimensional image of the structure of said steel reinforced concrete.

12. A method of obtaining a three-dimensional detailed image of the internal structure of steel reinforced concrete from a single source of penetrating radiation comprising the steps of:

a) exposing said steel reinforced concrete to penetrating radiation from a single source having a cross section of measurable dimensions;

b) placing radiation sensitive film on the opposite side of said steel reinforced concrete from said source to receive and record the attenuated radiation after passing through said concrete;

c) adjusting the exposure time so that shadows may be modulated by the thickness of steel within said concrete; and d) utilizing the dimensions of said source and making repeated summations of digitized information along multiple abscissas on said film to generate said three dimensional image of the structure of said steel reinforced concrete.

13. The method of claim 12, wherein said cross section has a source dimension in a direction parallel to said film, further comprising the step of determining said source dimension.

* * * * *